United States Patent [19]
Pero

[11] Patent Number: 6,020,351
[45] Date of Patent: Feb. 1, 2000

[54] CAROTENOID-NICOTINAMIDE-ZINC COMPOSITIONS AND METHODS OF TREATMENT USING SAME

[75] Inventor: Ronald W. Pero, Lund, Sweden

[73] Assignee: OXiGENE, Inc., Boston, Mass.

[21] Appl. No.: 09/011,332

[22] PCT Filed: Aug. 7, 1996

[86] PCT No.: PCT/US96/12790

§ 371 Date: Aug. 11, 1998

§ 102(e) Date: Aug. 11, 1998

[87] PCT Pub. No.: WO97/06790

PCT Pub. Date: Feb. 27, 1997

Related U.S. Application Data

[60] Provisional application No. 60/002,314, Aug. 14, 1995, abandoned.

[51] Int. Cl.$^7$ .................................................. A61K 31/455
[52] U.S. Cl. ......................... 514/355; 514/356; 514/419; 514/763; 514/762; 424/641; 424/643
[58] Field of Search ..................................... 514/763, 762, 514/355, 356, 419; 424/641, 643

[56] References Cited

U.S. PATENT DOCUMENTS

| | | |
|---|---|---|
| 5,162,369 | 11/1992 | Ashmead et al. . |
| 5,294,606 | 3/1994 | Hastings . |
| 5,310,554 | 5/1994 | Haigh . |
| 5,424,331 | 6/1995 | Shlyankevich . |

OTHER PUBLICATIONS

Rabinovitch et al., DNA Fragmentation is an Early Event in Cytokine–Induced Islet Beta–Cell Destruction, Chemical Abstracts, vol. 371, No. 8, Abstract No. 121:228605, 1994.

Jacobson et al., A Biomarker for the Assessment of Niacin Nutriture as a Potential Preventive Factor in Carcinogenesis, Chemical Abstracts, vol. 233, No. 1, Abstract No. 119:158939, 1993.

*Primary Examiner*—James H. Reamer

[57] ABSTRACT

Selectively administering to humans, as a daily dosage, a combination of carotenoids, nicotinamide (or niacin or a precursor thereof) and a source of zinc, in excess of normal dietary levels, for improving resistance to DNA damage, enhancing DNA repair capacity, and stimulating immune function.

13 Claims, 9 Drawing Sheets

CAROTENOID-NICOTINAMIDE-ZINC COMPOSITIONS AND METHODS OF TREATMENT USING SAME

This application claims benefit of provisional application No. 60/002,314 filed Aug. 14, 1995.

BACKGROUND OF THE INVENTION

This invention relates to new and improved compositions for and methods of treating humans and other animals to reduce DNA damage, enhance DNA repair capacity, and stimulate immune cellular function. More particularly, it relates to the administration to human (or other animal) subjects of a combination of carotenoid material, nicotinamide material, and zinc source material (all as hereinafter defined), e.g. as a drug treatment or a daily dietary supplement, and to compositions containing that combination of materials.

The term "carotenoid material" as used herein means carotenoids, such as material selected from the group consisting of alpha carotene, beta carotene, gamma carotene, lycopene and mixtures thereof. The term "nicotinamide material" as used herein means material selected from the group consisting of nicotinamide, niacin, tryptophane (an amino acid precursor to niacin synthesis) and mixtures thereof. The term "zinc source material" as used herein means an appropriate source of zinc for administration to humans and/or other animals, e.g. one or more zinc salts, such as zinc sulfate or other zinc salts like amino acids such as methionine or aspartate, dipeptides, gluconates, halides, nitrates, oxides or acetates.

In a specific aspect, the invention relates to a novel combination of naturally occurring carotenoid material, nicotinamide material and zinc source material as a combined treatment to aid patients in resisting cellular DNA damage such as oxidative damage, enhancing cellular DNA repair capacity and stimulating immune cellular function. In another specific sense, this combination of chemicals can be used as a dietary supplementation, or as a drug treatment, to prevent (or improve an individual's ability to resist) DNA damage, enhance DNA repair and stimulate immune function in diseases where these processes are central to the manifested disease state; e.g. ageing, cancer, cardiovascular disease and autoimmune disorders such as diabetes, rheumatoid arthritis and ulcerative colitis (Cross et al., Ann. Int. Med. 107:526–545, 1987; Harris, C. C., Cancer Res. 51(Suppl): 5023s–5044s, 1991; Olin, K. L. et al., Proc. Soc. Expt. Biol and Med. 203(4):461–466, 1993).

Carotenoids (Lupulescu, A., Int. J. Vit. Nutri. Res. 64(1): 3–14, 1993; Prabhala, R. H. et al., Ann. N. Y. Acad. Sci. 691:262–263, 1993; Chew, B. P. J., Dairy Sci. 76(9) :2804–2811, 1993; Santamaria, L. et al., J. Nutri. Sci. Vit. Spec. No:321–326, 1992; Machlin, L. J., Crit. Rev. Food Sci. and Nutri. 35 (1–2):41–50, 1995; Murakoshi, M. et al., Cancer Res. 52:6583–6587, 1992; Okuzumi, J. et al., Oncology 49:492–497, 1992), nicotinamide/niacin (Mandrup-Poulsen, T. et al., Diabetes Metabolism Rev. 9(4):295–309, 1993; Pero, R. W. et al., Biochimie, 77:385–393, 1995; Shockett, P. J., Immunol. 151(12):6962–6976, 1993; Boulikas, T., AntiCancer Res. 12(3):885–898, 1992; Brown, R. R., Adv. Expt. Med. Biol. 294:425–435, 1991; Henkin, Y. et al., Amer. J. Med. 91(3):239–246, 1991; Jacobsen, E. L., J. Am. Col. Nutri. 12(4):412–416, 1993) and zinc (Singh, A. et al., J. Appl. Physiology 76(6):2298–2303, 1994; Walsh, C. T. et al., Environmental Health Perspectives 102(Suppl. 2):5–46, 1994; Mocchegiani, E. et al., Blood 83(3):749–757, 1994; Singh, K. P. et al., Immunopharmacol, Immunotoxicol. 14(4):813–840, 1992; Mei, W. et al., Biol. Trace Element Res. 28(1):11–19, 1991; Chandra, R. K. et al., Clin. Lab. Med. 13(2):455–461, 1993) are each individually well recognized to possess disease preventive and immune stimulatory properties, even though they have never been combined with each other as a combination therapy, where they could prevent or delay human diseases and stimulate immune function (Compendium of Nonprescription Products, Canadian Pharmaceutical Association, 1994; Canadian Drug Identification Code, June 1995; The Extra Pharmacopoeia, Martindale, 30th edition; U.S. Pharmacopoeia Dispensing Information, 15th edition, 1995). Hence, it is not obvious from the scientific literature, or from availability of commercial products, that if one combines these agents above the normal dietary levels of carotenoids =as vit. A, 1467±1213 kcal, nicotinamide=33.1±26.7 mg, and zinc=6.8±8.4 mg (Payette, H., Am. J. Clin. Nutr. 52:927–932, 1990) having different mechanisms of action leading to the control of the same type of diseases, there could be achieved a formulation having potent properties in improving an individual's ability to resist cellular DNA damage, enhance cellular DNA repair and stimulate cellular immune function.

Humans have been selected over hundreds of thousands of years to respond to not one chemical but to a myriad of chemicals coming to us through our environment mainly thorough the diet. One can assume that our physiology is extremely well balanced to handle and process these chemical mixtures to extract as efficiently as possible the necessities of life such as nutritional energy sources and chemicals to maintain cellular homeostasis and reproduction. This has to be accomplished without introducing any toxicological consequences. Hence, it follows there is a reasonable likelihood that when humans see natural medicines above the levels normally found in the diet or environment, there exists a strong interaction between the megadoses of natural medicines, so that one supplement limits the uptake and metabolism of another, in an effort to provide a natural selection model by which humans can be protected from the toxicological consequences of overdosing. For example, the practice of prior art teaches that carotenoids and vitamins E or C are all radical (electrophilic) scavengers and that these natural products can be combined into supplements for additive biological effects. However, recent literature has not confirmed this practice based on scientific assumption because it was shown that these radical scavengers could inhibit each other's uptake and negate the desired induction of biological effects (Inform 6(7):778–783, 1995; Zhang et al., J. Clin. Nutr. 62:1477S–1482S, 1995; Niki et al., Am. J. Clin. Nutr. 62:1322S–1326S, 1995).

There are commercial products that are sold which have megadoses (i.e. above dietary levels) of carotenoids, nicotinamide and zinc offered in combination with each other, and in addition, they are formulated with several other chemically elucidated natural products. Two examples are given below:

Commercial Product I
("Radical Fighters ®," Twin Laboratories, Inc., Ronkonkoma, NY 11779 U.S.A.)

| | |
|---|---|
| Beta carotene (pro-vitamin A eq.) | 12500 IU |
| Vitamin C | 750 mg |
| Ascorbyl palmitate | 125 mg |

-continued

| | |
|---|---|
| Vitamin E (d-alpha tocopherol) | 250 IU |
| L-cysteine | 250 mg |
| L-glutathione (reduced) | 12.5 mg |
| Selenium (selenite) | 100 mcg |
| Zinc (gluconate) | 10 mg |
| Vitamin B-1 | 75 mg |
| Vitamin B-2 | 50 mg |
| Nicotinamide | 50 mg |
| Niacin | 25 mg |
| Vitamin B-5 | 250 mg |
| Vitamin B-6 | 62.5 mg |
| Vitamin B-12 | 150 mcg |
| Folic acid | 200 mcg |
| Biotin | 75 mcg |
| PABA (para-aminobenzoic acid) | 150 mg |
| Inositol | 100 mg |
| Choline | 100 mg |

Commercial Product II
(Vitamins for Women, Bonne Forme, 4250 Hempstead Tpke,
Suite 21, Bethpage, NY 11714 USA)

| | |
|---|---|
| Vitamin A | 5000 IU |
| Beta carotene | 3 mg |
| Vitamin D-3 | 400 IU |
| Vitamin E | 200 IU |
| Vitamin K | 10 mcg |
| Vitamin C | 500 mg |
| Vitamin B-1 | 10 mg |
| Vitamin B-2 | 10 mg |
| Vitamin B-6 | 50 mg |
| Niacin | 50 mg |
| Folic acid | 400 mcg |
| Vitamin B-12 | 50 mcg |
| Biotin | 50 mcg |
| Pantothenic acid | 20 mg |
| Calcium | 1000 mg |
| Magnesium | 300 mg |
| Potassium | 40 mg |
| Iron | 9 mg |
| Zinc | 15 mg |
| Copper | 1 mg |
| Manganese | 5 mg |
| Iodine | 50 mcg |
| Chromium | 80 mcg |
| Selenium | 50 mcg |
| Molybdenum | 10 mcg |

However, these commercial products do not establish or make obvious that the specific combination of carotenoids, nicotinamide and zinc is effective at reducing cellular DNA damage induction or enhancing DNA repair and immune function. On the contrary, as demonstrated below, applicant herein has now found that the administration of carotenoids, nicotinamide and zinc in combination with other natural medicines or nutrients such as the Commercial Product I referred to above does not reduce cellular DNA damage induction or enhance DNA repair and immune function as has been assumed but not proven in the prior art. This discovery is also consistent with the prior art (Inform 6(7):778–783, 1995; Zhang et al., J. Clin. Nutr. 62:1477S–1482S, 1995; Nidi et al., Am. J. Clin. Nutr. 62:1322S–1326S, 1995) which has confirmed that the natural products (e.g. medicines or nutrients) having similar modes of biochemical action have been shown to block each other's uptake and absorption, thus resulting in altered biological functions. It follows then although not practiced in the prior art that it cannot be assumed supplementing an a priori combination of natural products above dietary levels will result in additive biological effects of each product administered separately without previously establishing the lack of inhibition of natural products supplemented in combination.

The exact mechanism of action of carotenoids such as beta carotene is not fully understood but it is commonly accepted scientifically that one primary mechanism is to scavenge oxygen derived free radicals produced either as by-products of metabolism or from exogenous environmental exposures (Lieber, D. C., Ann. N. Y. Acad. Sci. 691:20–31, 1993; Bohm, F. et al., J. Photochem. Photobiol. 21(2–3):219–221, 1993; Regnault, C. et al., Ann. Pharmacotherapy 27(11):1349–1350, 1993). As a free radical scavenger, carotenoids can be expected to reduce or protect against the chemical damage induced in DNA, RNA and protein of cells by toxic environmental exposures or endogenous cellular metabolic errors that ultimately can result in a disease state. On the other hand, nicotinamide and zinc salts do not possess this chemical property which results in an improved biological cellular function.

Nicotinamide and its metabolic equivalent nicotinic acid (niacin, vitamin $B_3$) or even tryptophane which is the synthetic precursor to niacin is the main precursor for the formation and maintenance of the cellular pool of NAD (Bernofsky, Mol. Cell. Biochem. 33:135–143, 1980; Olsson, A. et al., Biochem. Pharmacol. 45:1191–1200, 1993). NAD is essential for cellular ATP production and maintenance of the cell's redox potential, and it is also the substrate for the DNA repair enzyme, poly ADP-ribosyl transferase (ADPRT). Niacin deprivation decreases the NAD pools significantly both in tissue culture cells (Jacobson, E. et al., IN: ADP-Ribosylation Reactions (Poirier, G. G. and Moreau, P., eds.), pp. 153–162, Springer Verlag, New York, N.Y., 1992), and animal systems (Zhang et al., J. Nutri. 123:1349–1355, 1993) as well as humans (Fu et al., J. Nutri. 119:1949–1955, 1989). The depleted cells have an increased sensitivity to DNA damage and the levels of poly(ADP-ribose) production in cultured cells (Jacobson, E. L., as cited, 1992) or in rat liver (Rawling et al., J. Nutri. 124:1597–1603, 1994) were significantly lower after mild nicotinamide deficiency. On the other hand, when niacin was given as a supplement to ordinary nutrition (i.e. above known dietary levels) the NAD pool increased and the cells were less sensitive to oxygen radicals (Weitberg, A. B., Mutational Res. 216:197–201, 1989). Therefore, it is obvious from this review of the prior art that the primary mechanism of action of nicotinamide/niacin differs from carotenoids and zinc in that the cell's potential for energy metabolism is increased by amplifying NAD and ATP pool supplies (i.e. these biochemicals are the energy sources of living organisms) which in turn is useful to cells, tissues and organs to reduce DNA damage, enhance DNA repair (i.e. poly ADP-ribosylation) and stimulate immune function where the relevance to the disease state is apparent (Pero, R. W. et al., Biochimie 77:385–393, 1995).

Zinc differs from the carotenoids and nicotinamide with regard to its mechanism of action in that it influences disease development and immune function by being an essential co-factor in several enzyme functions involving replication, DNA repair and antioxidant defense of cells. Zinc is required for cell replication and DNA polymerase activity (Williams, R. O. et al., J. Cell Biol. 58:594–601, 1973). There are two zinc fingers in the DNA binding domain of the poly adenosine diphosphate ribosyl transferase (ADPRT) gene and other DNA repair proteins (Dawat, P. et al., Microbiol. 141 (Pt 2):411–417, 1995; Matsuda, T. et al., J. Biol. Chem. 270(8):4152–4157, 1995; Chiriccolo, M. et al., Mutation Res. 295(3):105–111, 1993) which contain cysteine residues (i.e. an amino acid), and if these cysteine residues are oxidized at their thiol constituents, they would prevent DNA binding and participation in DNA repair (Mazen et al., Nucleic Acid Res. 17:4689–4698, 1989; de Murcia, G. et al., BioEssays 13(9):455–462, 1989; Pero, R. W. et al., Biochimie 77:385–393, 1995; Althaus, F. et al., Mol. Cell. Biochem. 138(1–2):53–59, 1994). Moreover, superoxide dismutase is an antioxidant enzyme protecting cells from the harmful superoxide anion because this radical is a substrate for the enzymatic reaction that also requires zinc as a cofactor (Brunori, M. and Rotilio, G., Methods in Enzymology 105:22–35, 1984).

In summation, even though carotenoids, nicotinamide/ niacin and zinc have been shown to have some enabling utility in cell and animal models as single agents in the prevention of certain diseases and in the stimulation of immune function, there has been a lack of corresponding, consistent data in humans (Bodgen, J. D. et al., Amer. J. Clin. Nutri. 48:655–663, 1988; Walsh, C. T. et al., Environmental Health Perspectives 102(Suppl. 2):5–46, 1994). In addition, it is not possible for one skilled in the art to a priori predict whether agents with different mechanisms of action will be synergistic, additive or inhibitory to the biological response they will elicit when given in combination.

SUMMARY OF THE INVENTION

The present invention, in a first aspect, broadly contemplates the provision of a composition of matter for administration to humans or other animals consisting essentially of a combination of carotenoid material, nicotinamide material and zinc source material and essentially free of other active ingredients. By "consisting essentially of" and "essentially free of other active ingredients" is meant that the composition contains no active nutrient agents other than the aforementioned carotenoid material, nicotinamide material and zinc source material. The term "active nutrient agents" is employed herein as a generic designation for vitamins, minerals and other substances serving as anti-oxidants, anti-oxidant co-factors, or otherwise contributing to disease prevention, inhibition of DNA damage, improvement of DNA repair capacity, and/or enhanced immune function, such as have heretofore been sold in concentrated, isolated, or combined form as dietary supplements and the like for human and/or animal consumption. In particular, the term "active nutrient agents" specifically includes the above-listed ingredients of the two products identified above as Commercial Product I and Commercial Product II.

Stated in other words, then, the invention in this aspect embraces compositions containing carotenoid material, nicotinamide material and zinc source material, and no other active nutrient agents. The compositions of the invention may be embodied in formulations for oral administration, or alternatively, in formulations for parenteral administration.

In illustrative or preferred practice of the invention, the carotenoid material may be selected from the group consisting of alpha carotene, beta carotene, gamma carotene, lycopene and mixtures thereof; the nicotinamide material may be selected from the group consisting of nicotinamide, niacin, tryptophane and mixtures thereof; and the zinc source material may be one or more zinc salts.

For human administration, the carotenoid material, nicotinamide material and zinc source material may be present in proportions effective, in combination, to improve resistance to DNA damage, enhance DNA repair capacity, and stimulate immune function in a human subject to whom the composition is administered as a daily dosage.

The invention also contemplates the provision of a method of treating a human or other animal subject, consisting of administering carotenoid material, nicotinamide material and zinc source material to the subject to selectively supplement the subject's dietary intake thereof (i.e., without supplementing the dietary intake of any other active nutrient agents) and repeating the administration on a substantially daily basis.

Thus, in a particular sense, the invention contemplates the provision of a method of treating a human subject consisting of selectively administering to the subject carotenoid material, nicotinamide material and zinc source material in daily dosage amounts effective, in combination, to improve resistance to DNA damage, enhance DNA repair capacity, and stimulate immune function. In a specific example of currently preferred dosage range for humans, about 100 mg of carotenoid material, about 100 mg of nicotinamide material and about 10 mg of zinc source material are administered daily in this method.

From a theoretical standpoint, this invention is based on a principle of combining chemical products which are individually known to possess either cancer preventive or immune stimulatory properties into one formulation which contains only active components where at least one mechanism of action for each active component is known to be different from the known mechanisms of action of the other components. So far as applicant is aware, this principle has not heretofore been recognized in the art.

The invention involves the discovery that natural products should not be combined into a natural medicine unless one tests whether each ingredient is additive to the overall desired biological effect, and that one way to accomplish this endpoint is to not combine natural products that have similar modes of action and thus competitive routes of absorption and excretion without first testing the combination for additive effects. That is to say, the present invention avoids inhibited uptake and absorption of natural products, thereby obtaining additive biological effects, by combining only natural products having well defined different and thus potentially non-competitive modes of action which is, for example, the case with the exclusive combination of carotenoids+nicotinamide+zinc.

Thus, in particular, it has now been found that when the combination of carotenoids+nicotinamide+zinc in accordance with the invention was administered to humans, there was a statistically significant reduction in oxidative cellular DNA damage, an enhancement in DNA repair capacity and a stimulation in immune function. These data support that by combining these agents above the concentrations found in the normal diet, and which have different known mechanisms of action at stimulating immune function, the combination treatment results in a more consistent pattern and thus an additive influence on biological responsiveness.

The practice of this invention involves supplementing humans or animals for example, by the oral, intraperitoneal, intravenous, subcutaneous or intramuscular routes of administration with the combination of carotenoids+nicotinamide/ niacin+an appropriate zinc salt at a dose of this combination that exceeds a normal dietary suppplementation. The practice of the prior art teaches that dietary supplementation containing this combination together with simultaneous supplementation of other nutrients and/or natural products cannot enhance immune function (Payette, H. et al., Am. J. Clin. Nutr. 52:927–932, 1990; Zhang et al., J. Clin. Nutr. 62:1477S–1482S, 1995) but when carotenoids (as Caroplex, C. E. Jamieson, Ltd., Ontario, Canada), nicotinamide and a zinc salt are given alone in the absence of other natural supplements above dietary levels, e.g. 100 mg, 100 mg and 10 mg by oral daily administration over a 7 week period, respectively, the resistance to oxidative cellular DNA damage, and enhancement of DNA repair and immune function were observed.

The clinical evaluation was determined by comparing each individual's biological response before and after supplementation. In such a manner, each individual became his own control; e.g. the male subjects were given baseline measurements of resistance to cellular DNA damage, enhancement of DNA repair and stimulation of immune function once a week for 4 weeks, and then they were supplemented daily and the same measurements repeated once a week for the last 5 weeks of a 7 week intervention period. The before measurements (i.e. n=4) were the baseline biological response parameters to be compared to the after measurements (i.e. n=5). One individual was not supplemented to provide a control for the supplemented individuals. The data from this experimental design has taught that resistance to cellular DNA damage, enhancement of DNA repair and stimulation of immune function are all significantly modulated by a combination of carotenoids+nicotinamide+zinc when administered as an exclusive drug combination above dietary levels, but not when co-administered together with other additional nutrient or natural product supplements.

Further features and advantages of the invention will be apparent from the detailed description hereinbelow set forth, together with the accompanying drawings.

DETAILED DESCRIPTION

Figure 1:
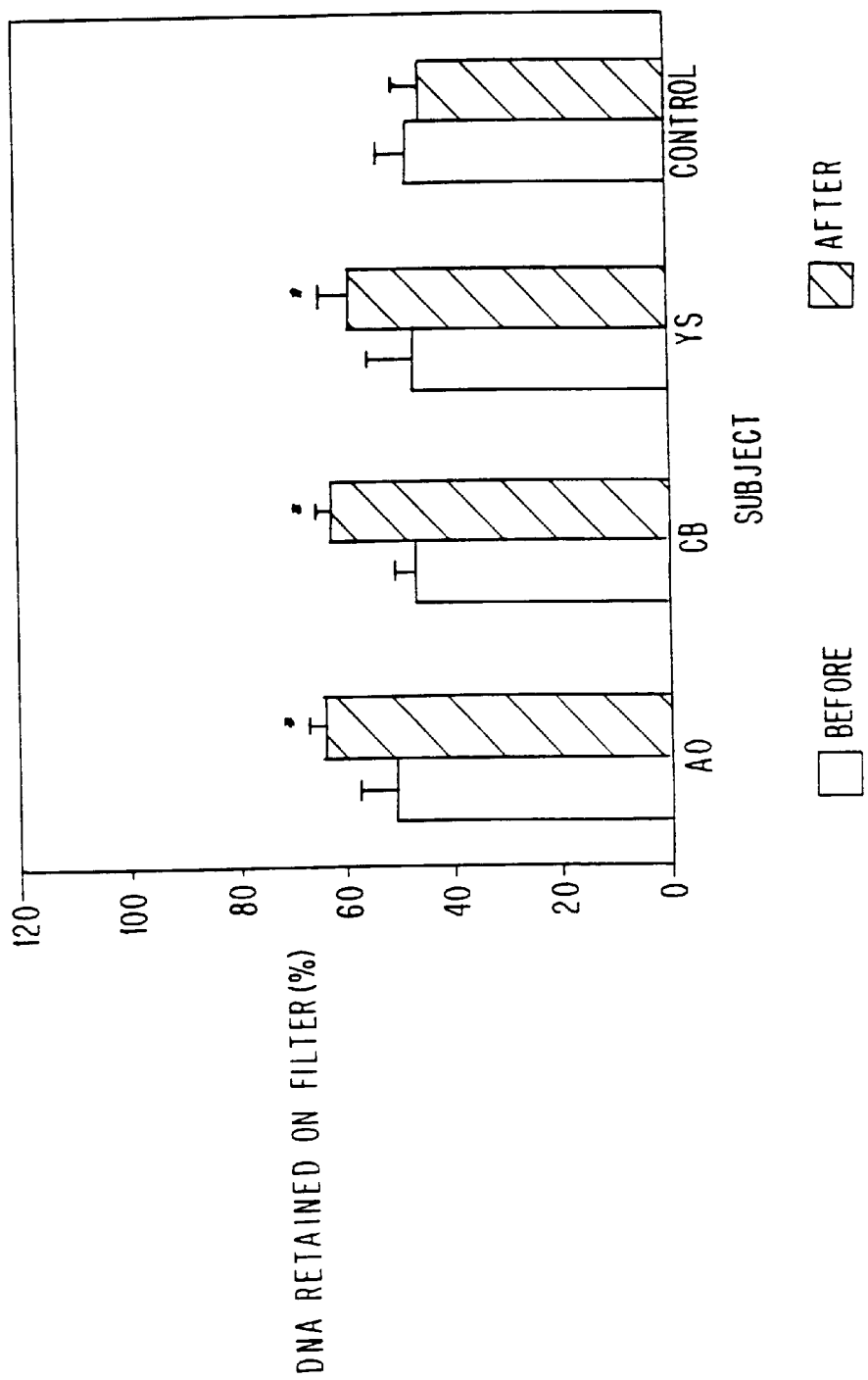
FIG. 1 is a bar graph representing DNA single strand breaks induced by 100 $\mu$M hydrogen peroxide, assessed by alkaline elution in HML before and after supplementation of the natural products carotenoids+nicotinamide+zinc in accordance with the present invention. Data are shown as mean and SD. *$p<0.05$ compared with the value before supplementation.

In the specific embodiment hereinafter described in detail, this invention involves the use of a combination consisting essentially of carotenoids+nicotinamide+zinc gluconate (and no other active nutrient agents) as an oral supplement, over and above the normal levels of these components in the diet, administered daily to increase an individual's resistance to cellular DNA damage, enhance cellular DNA repair and stimulate immune cell responsiveness in vivo. The design of the study to prove this invention was based on combining substances with known properties to prevent cancer and stimulate immune function but with differing mechanisms of action; e.g. carotenoids=electrophilic scavenger of radicals produced endogenously by cells or exogenously by the environment, nicotinamide=amplified source of energy via increased production of NAD or ATP, and zinc=an essential cofactor to antioxidant, replicative and DNA repair enzymes in cells. The hypothesis was that since none of these substances have produced consistent effects in humans as a single administered agent, this shortcoming could be overcome when administered in combination because these substances might produce a consistently additive chemo-preventive biological response because of non-competitive modes of action instead of, for example, an inhibited one.

There were 4 healthy male volunteers age 30–40 years and working in a similar environment included into this study to establish the validity of this invention. The baseline evaluation of human mononuclear leukocytes (HML)

responses before in vivo supplementation of (i) resistance to cellular DNA damage determined by alkaline DNA elution, (ii) enhancement of DNA repair determined by the repairability of a standardized dose of hydrogen peroxide, and (iii) the stimulation of immune function determined by phytohemagglutinin (PHA) mitogenic stimulation were each carried out once per week for 4 consecutive weeks. Three of the subjects were given oral administration of carotenoids, nicotinamide and zinc gluconate as described below on a daily basis for 7 consecutive weeks and each of the biological response endpoints were determined once per week for the last 5 weeks. One subject received no supplementation for the 7 week intervention period but he was sampled and bioassayed for the desired biological response endpoints consecutively once per week for the last 5 week period, and this subject served as a "no supplementation" control. The individual values for the "before" and "after" supplementation periods were then combined and compared statistically as groups for assessment of the treatment or no treatment affects.

The drugs used were supplied by C. E. Jamieson, Ltd. (Ontario, Canada) as carotenoids=Caroplex as 100 mg soft gel capsules, nicotinamide=100 mg tablets and zinc gluconate=10 mg tablets, and the combination of these three substances, embodying the present invention, is hereinafter sometimes referred to as "CNZ." Caroplex is a proprietary manufactured natural source of carotenoids from palm oil containing beta carotene=60%, alpha carotene=34%, gamma carotene=3% and lycopene=3% (Iwasaki, R. and Murakoski, M., Inform 2(2):210–217, 1990). These three drugs were given together during the same period by oral administration Monday through Sunday (daily) for a 7 week period. Compliance was always <3 missed daily administrations per subject during the treatment phase.

In order to test the hypothesis that carotenoids, nicotinamide and zinc (CNZ) when given in combination but in the presence of other nutrient or natural medicine supplements would not result in increasing an individual's resistance to cellular DNA damage or enhancing DNA repair and immune function, the same individuals supplemented with CNZ were given a "no intervention" period for 13 weeks, the baseline values re-established over a 4 week period for the biomarkers used in the CNZ study, oral supplementation of the aforementioned Commercial Product I (hereinafter sometimes referred to as "CPI") for 6 consecutive weeks was initiated together with a "no intervention" control, and the biomarkers were determined once per week for the last 4 weeks. CPI contained 20 ingredients including carotenoids, nicotinamide and zinc, and they were supplemented daily at the concentrations for each individual component as indicated in the table set forth above under the heading "Commercial Product I." Compliance was again always <3 missed daily administrations per subject during the treatment phase, except for Case A who had acute appendicitis just at the initiation of the CPI intervention, and hence this subject was converted to a "no intervention" control.

Each week about 20 ml venous blood was collected into 2 heparinized vacutainers (143 U.S.P. Units/10 ml tube) and HML, erythrocytes, and plasma samples were separated according to the method described by Pero et al. (J. Int. Med 233:63–67, 1993). HML at a density of $2 \times 10^6$ cells/ml were suspended in 10% fresh autologous plasma supplemented RPMI 1640 medium. This culture medium was used throughout all the experiments. DNA single strand breaks by alkaline elution, poly ADPRT activity, NAD pool determinations by high pressure liquid chromatography (HPLC) and phytohemagglutinin (PHA) induced mitogenic response in HML were prepared for analysis immediately after blood sampling. The other unused samples were frozen at $-70°$ C. for future analyses.

Oxidative DNA damage and DNA repair were analyzed by alkaline elution using HML exposed on ice to zero or a standard dose of 100 $\mu$M $H_2O_2$ for 60 minutes and then the cells were allowed to be incubated at 37° C. for 0, 30 or 60 minutes in order to carry out DNA repair. DNA damage and repair at the different time points were measured by alkaline elution as described by Kohn and coworkers (in Friedberg, E. C. and Hanawalt, P. (eds.), DNA Repair: A Laboratory Manual of Research Procedures, Marcel Dekker, New York, pp. 379–402, 1981) with modifications to measure the unlabelled DNA by microfluorometry (Cesarone, C. F. et al., Anal. Biochem. 100:188–197, 1979).

The DNA repair enzyme, poly ADPRT, was assayed by the permeabilized cell technique procedure of Berger with modifications as previously described (Pero et al., Carcinogensis 10:1657–1664, 1989). Poly ADPRT activities both in the constitutive or induced physiological state were measured on $1 \times 10^6$ HML exposed or not to a standardized dose of 100 $\mu$M $H_2O_2$ at 37° C. for 30 min. and then the cells were harvested by centrifugation, permeabilized, and poly ADPRT activity determined by radiometric procedures as described in detail elsewhere (Pero et al., Carcinogenesis 10:1657–1664, 1989).

For NAD determinations by HPLC, frozen erythrocyte packed pellets (500 $\mu$l) were thawed in 600 $\mu$l 1.8 M perchloric acid (PCA) on ice. After homogenization and addition of 25 $\mu$l 2.4 mM thymidine (dThd) as an internal standard, the samples were centrifuged at 14,000 g to remove insoluble material. The supernatant (0.5 ml) was neutralized by addition of 150 $\mu$l 2 M $K_2CO_3$ solution. After another centrifugation at 14,000 g the supernatant was ready for analysis by HPLC. Chemicals used for buffer solutions were of analytical grade, and the elution buffer was 150 mM potassium phosphate, pH 6, containing 0–4% methanol (v/v) (Jones, D. P., J. Chromatogr. 225:446–449, 1981). The elution buffer was filtered through a 0.2 $\mu$M sterile polysulfone filter (VacuCap, Gelman Sciences, Ann Arbor, Mich.) prior to use. The NAD analysis was performed in a 3 micron $C_{18}$ column (83 mm$\times$4.3 mm i.d, Perkin Elmer Corp. Norwalk, Conn.) with a four pump Perkin Elmer (410 LC) system having a variable UV detector (LC-95) and an integrator (LCI-100). Baseline separation was obtained within <12 min., when a water solution containing ADP-ribose, AMP, NADP, NAM, NAD, and dThd was analyzed. The general operating conditions were as follows: flow rate=1.0 ml/min; mobile phase=1.4% methanol for 3.5 min. and 4% for 10 min.; temperature=20–25° C.; recycling time between runs=10 min.; detection at 254 nm. A standard curve was prepared from frozen erythrocyte samples which were incubated for 1.5 hours at 37° C. before extraction with PCA followed by addition of 0–40 $\mu$M NAD. The NAD concentration in the samples was determined as a function of the peak height of NAD divided with the peak height of the internal standard (dThd).

The phytohemagglutinin (PHA) induced mitogenic response was assayed using $2 \times 10^5$ HML incubated in microculture plates containing 200 $\mu$l RPMI 1640 supplemented with 10% autologous plasma and 6 $\mu$l PHA/ml (Gibco) at 37° C. and 5% $CO_2$ for 4 days (Pero et al., Biochimie 77:385–393, 1995). After two additional days more of incubation in the presence of [$^3$H]-thymidine (final concentration 6 Ci/mmol, 1 $\mu$Ci/ml), the cells were harvested and assayed for content of bound [$^3$H]-thymidine radiolabelled material per $2 \times 10^5$ HML.

The following examples are given for the purpose of illustrating the present invention:

EXAMPLE 1

This example demonstrates the effectiveness of treating subjects per os with carotenoids (100 mg as Caroplex)+nicotinamide (100 mg)+zinc gluconate (10 mg) (CNZ) on a daily basis for 7 consecutive weeks and then analyzing this intervention for protecting individuals from the DNA damaging effects of oxidative damage (e.g. 100 $\mu$M $H_2O_2$) in human mononuclear leukocytes (HML). These data teach that the 3 subjects supplemented as described above all had significant (p<0.05) increases in their HML's ability to resist $H_2O_2$ induced DNA damage, whereas the control subject who had only dietary supplementation of these agents during the intervention period was unaffected with regard to this biological response parameter (FIG. 1).

EXAMPLE 2

Figure 2:
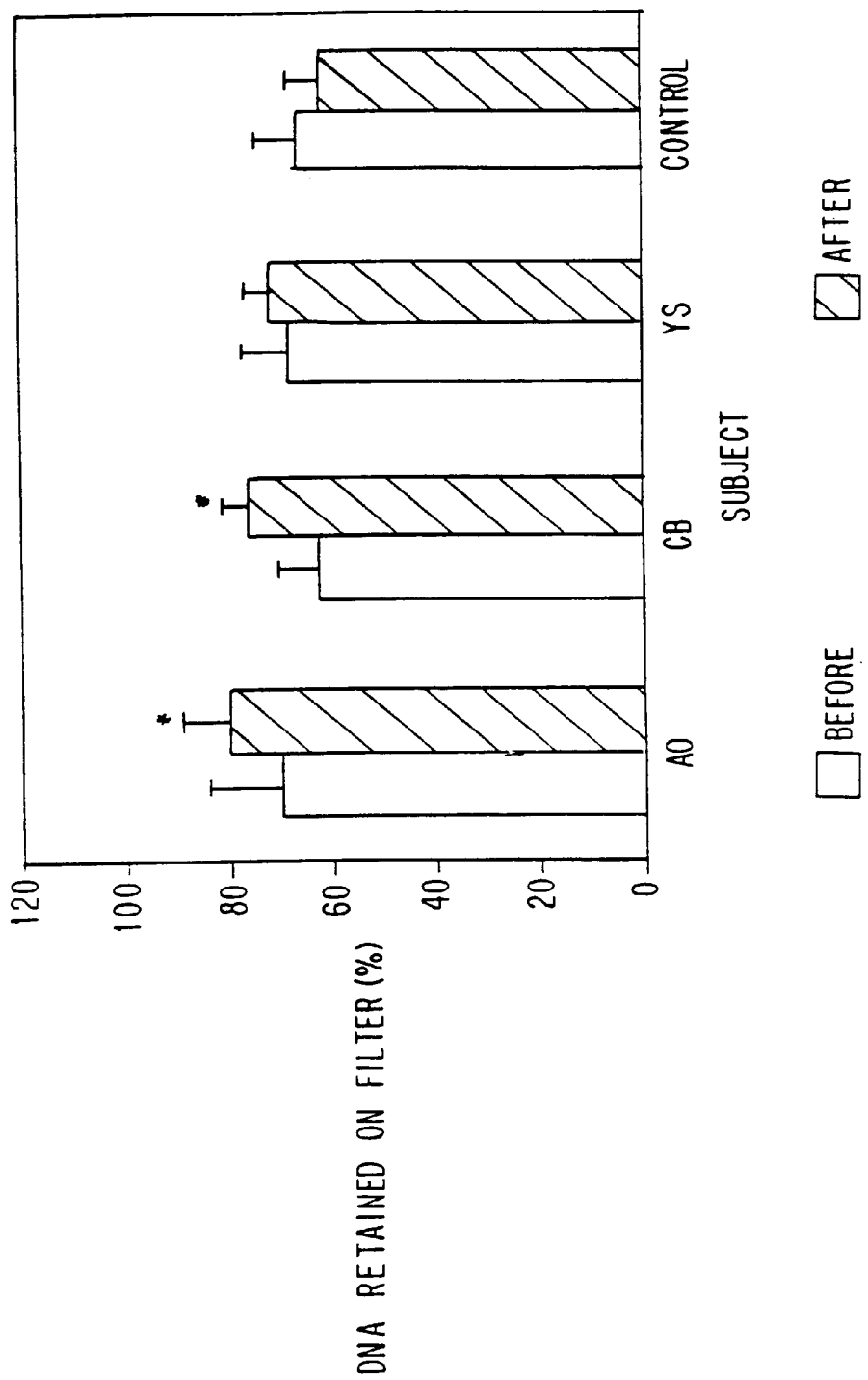
FIG. 2 is a bar graph representing DNA repair 30 minutes after induction of DNA strand breaks by 100 $\mu$M hydrogen peroxide in HML, evaluated by alkaline elution before and after the supplementation of the natural products carotenoids+nicotinamide+zinc in accordance with the present invention. Data are shown as mean and SD. *$p<0.05$ compared with the value before the supplementation.
Figure 3:
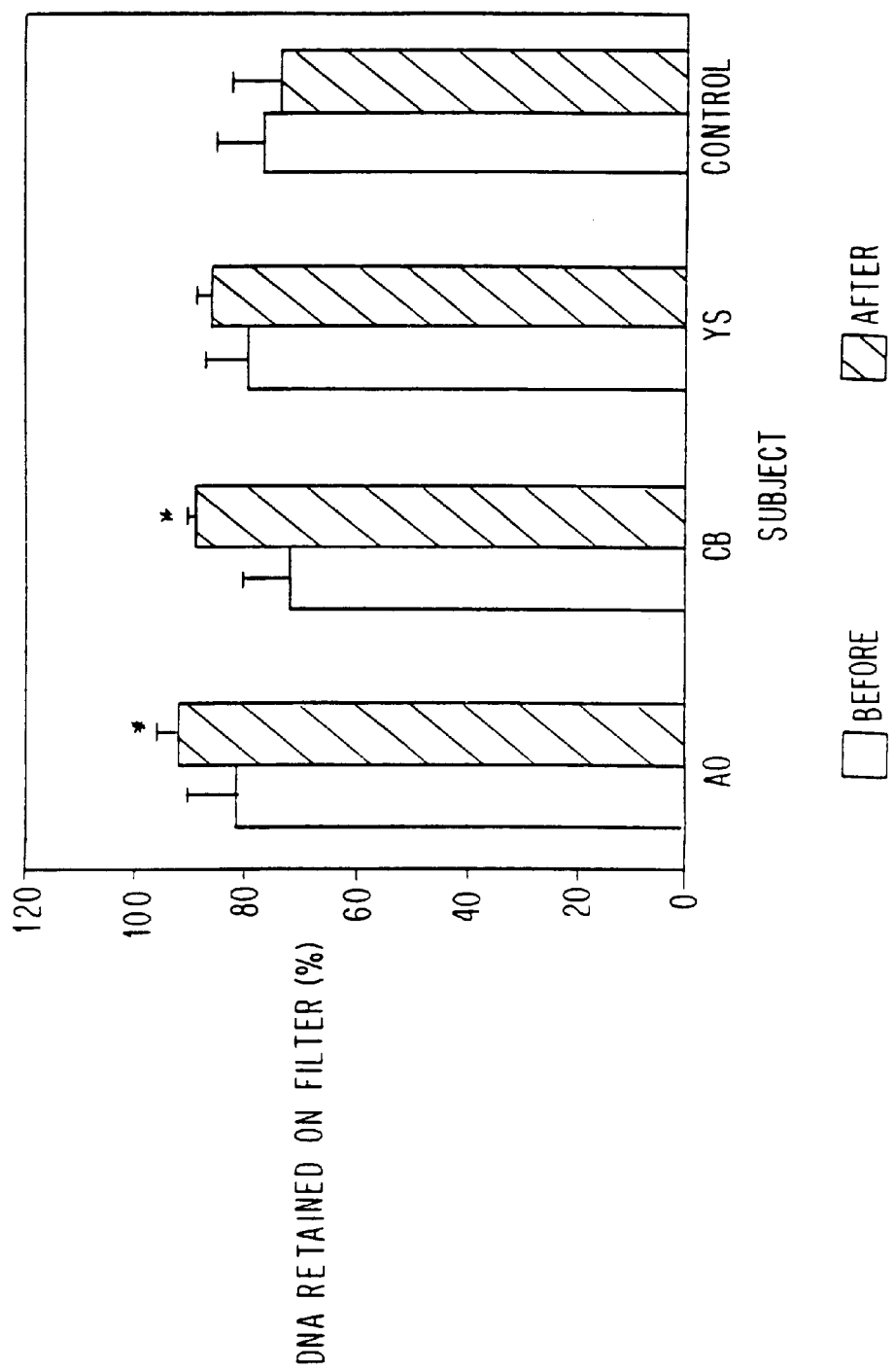
FIG. 3 is a bar graph representing DNA repair 60 minutes after induction of DNA strand breaks by hydrogen peroxide in HML, evaluated by alkaline elution before and after supplementation of the natural products carotenoids+nicotinamide+zinc in accordance with the present invention. Data are shown as mean and SD. *$p<0.05$ compared with the value before supplementation.

This example discloses the effectiveness of treating subjects per os with carotenoids (100 mg as Caroplex)+nicotinamide (100 mg)+zinc gluconate (10 mg) (CNZ) on a daily basis for 7 consecutive weeks for the purpose of enhancing an individual's DNA repair in HML treated in vitro with oxidative DNA damage (i.e.100 $\mu$M $H_2O_2$). The results showed that subjects receiving supplementation had a significantly increased (p<0.05) DNA repair of 100 $\mu$M induced DNA damage after 30 min. and 60 min. DNA repair time whereas the non-supplemented control subject who had only dietary levels of these agents was not significantly altered during the intervention period (FIGS. 2–3).

EXAMPLE 3

Figure 4:
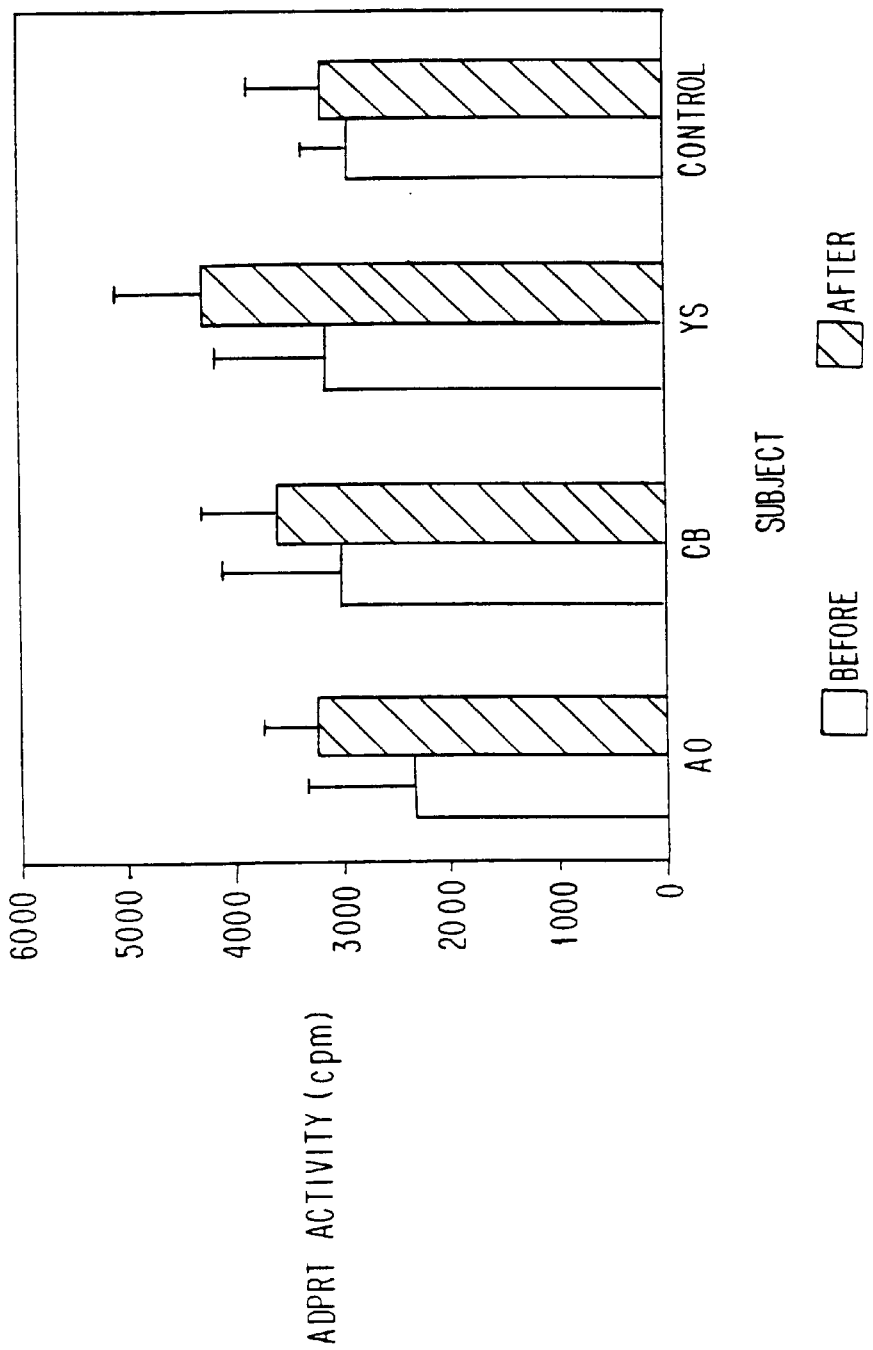
FIG. 4 is a bar graph representing the poly ADPRT activity in HML before and after supplementation of the natural products carotenoids+nicotinamide+zinc in accordance with the present invention. Data are shown as mean and SD. *$p<0.05$ compared with the value before supplementation.

This example supports the data already presented in Examples 1–2 and deals with the assessment (quantification) of the DNA repair enzyme, poly ADPRT, before and after in vivo per os daily individual supplementation with carotenoids (100 mg as Caroplex), nicotinamide (100 mg) and zinc gluconate (10 mg) (CNZ) for 7 consecutive weeks. The data indicate that poly ADPRT activity was enhanced to a greater extent by the intervention than was the control subject who received no supplementation during the intervention period (FIG. 4). Although this data did not reach statistical significance, it adds to the knowledge already taught in Examples 1–2, which showed that this intervention of drugs caused a reduction in oxidative cellular DNA damage, and at the same time, the cells could repair the DNA damage much better.

EXAMPLE 4

Figure 5:
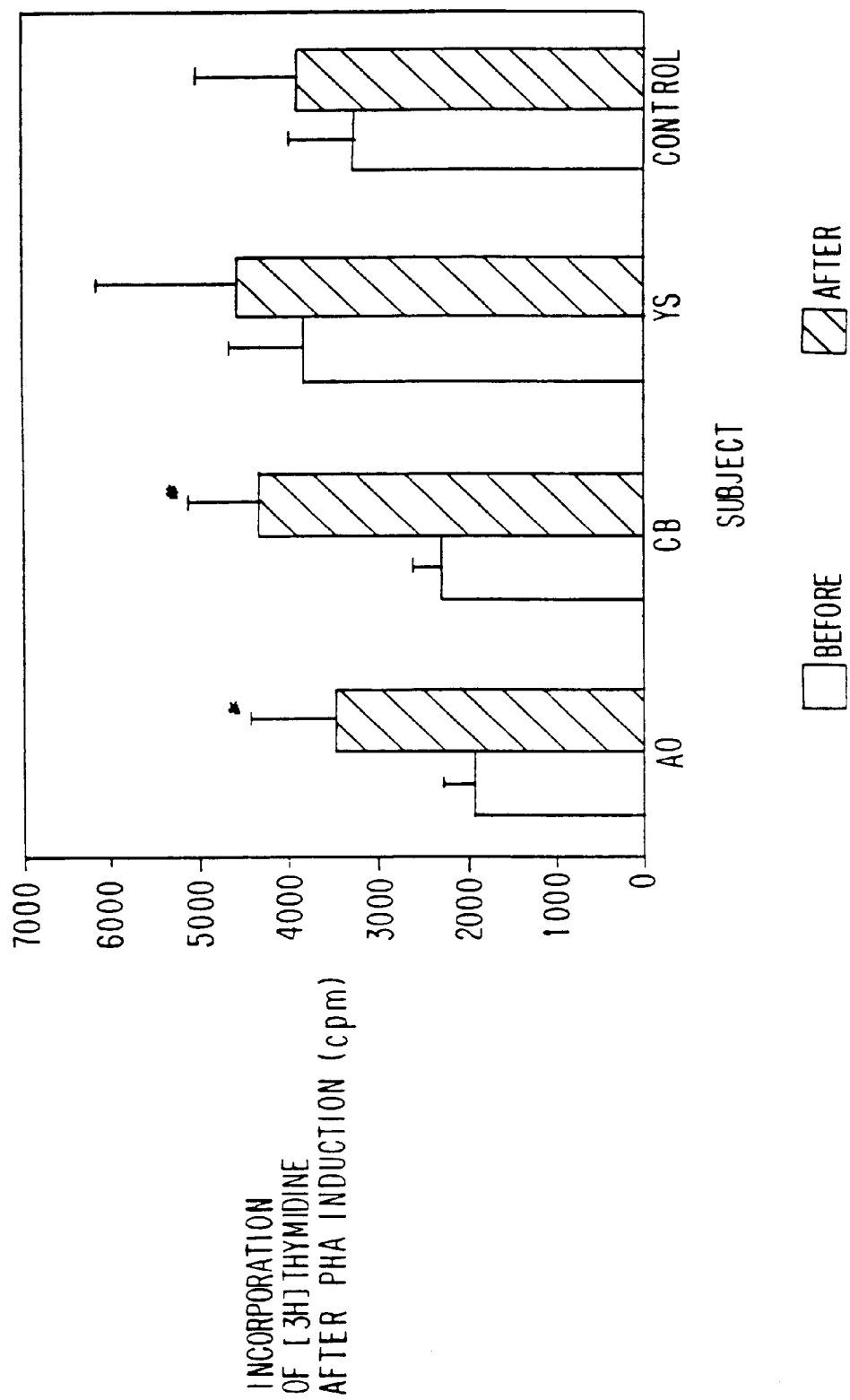
FIG. 5 is a bar graph representing the incorporation of [$^3$H]-thymidine after PHA mitogenic induction in HML before and after supplementation of the natural products carotenoids+nicotinamide+zinc in accordance with the present invention. Data are shown as mean and SD. *$p<0.05$ compared with the value before supplementation.

This example discloses the effectiveness of treating individuals with nicotinamide when the nicotinamide (100 mg) was administered per os on a daily basis for 7 consecutive weeks with carotenoids (100 mg as Caroplex) and zinc gluconate (10 mg) (CNZ) when evaluated by the effects on the NAD energy pools. The data presented in FIG. 5 clearly show that nicotinamide supplementation has significantly expanded the NAD cellular concentration of erythrocytes, and thus by comparison, the ability to reduce DNA damage and enhance DNA repair in HML as was observed in Examples 1–3 of this same study. Erythrocytes have also been shown to be a good overall indicator of NAD status in nucleated cells (Jacobson, E. L. et al., in: ADP-Ribosylation Reactions (Poirier, G. G. and Moreau, P., eds.), pp. 153–162, Springer-Verlag, New York, N.Y. 1992). This example also teaches that the presence of carotenoids and zinc in the supplementation did not block or inhibit the biological response of enhanced NAD pools that has been observed in the literature when nicotinamide was supplemented by itself.

EXAMPLE 5

Figure 6:
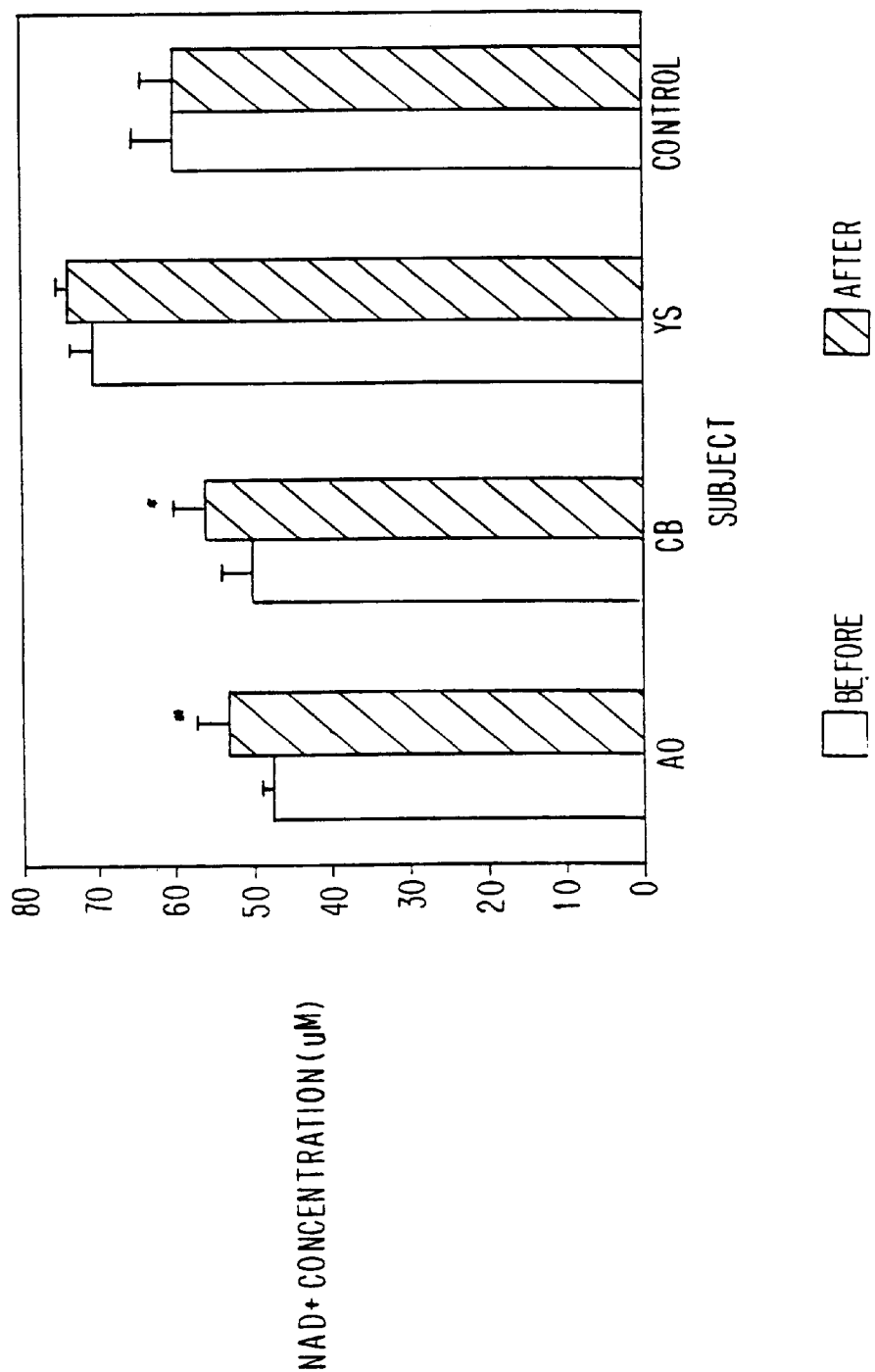
FIG. 6 is a bar graph representing the NAD concentrations in human erythrocytes before and after the supplementation of the natural products carotenoids+nicotinamide+zinc in accordance with the present invention. Data are shown as mean and SD. *$p<0.05$ compared with the value before supplementation.

This example involves the assessment of phytohemagglutinin (PHA) mitogenic stimulation of HML as an immune function test before and after per os daily supplementation of carotenoids (100 mg as Caroplex), nicotinamide (100 mg) and zinc gluconate (10 mg (CNZ) for 7 consecutive weeks. The data demonstrate that individuals receiving the intervention treatment had an enhanced PHA-induced mitogenic response as evidenced by the increased [$^3$H]-thymidine incorporation into HML than did the one subject who was evaluated by the immune function test during the last 5 weeks of the intervention period but did not receive any supplementation (control) (FIG. 6). Moreover, when these data are combined with the data presented in Examples 1–4, they teach that when immune function is enhanced it is paralleled and mechanistically linked to an approved ability of HML to resist oxidative DNA damage (Examples 1, 4) and to enhance DNA repair (Examples 2, 3).

EXAMPLE 6

Figure 7:
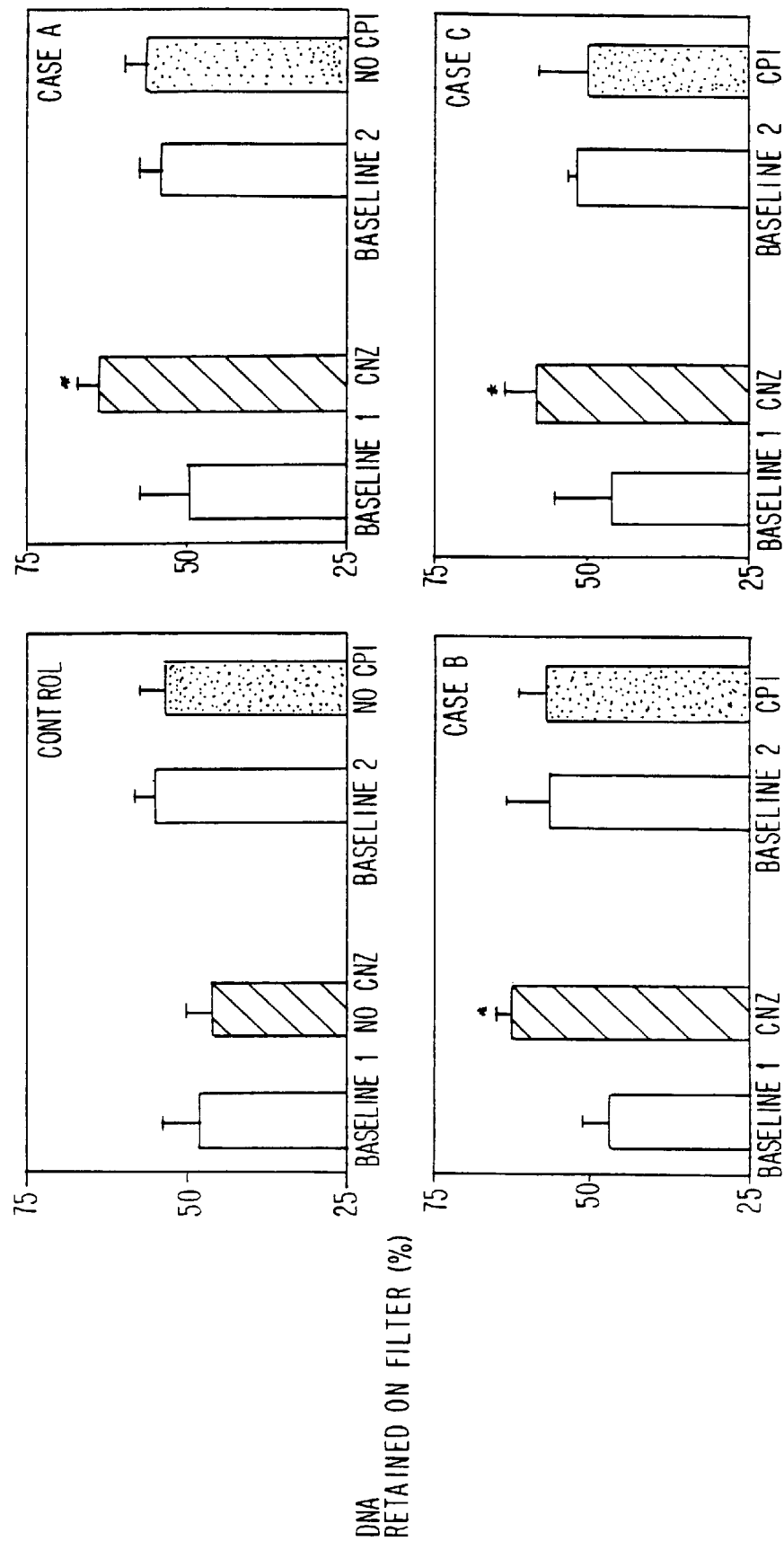
FIG. 7 is a set of bar graphs comparing the in vivo effect of carotenoids+nicotinamide+zinc supplementation in accordance with the invention ("CNZ"), and the aforementioned Commercial Product I supplement ("CPI"), on DNA damage in human mononuclear leukocytes. The DNA damage was induced by 100 $\mu$M hydrogen peroxide as assessed by alkaline elution. The data are expressed as mean in column and SD by error bar (n=4 to 5). * indicates a significant difference ($p<0.05$, t-test) compared with corresponding baseline level. § Note: Case A was not supplemented with Commercial Product I because of acute appendicitis just as the supplement started, and no blood sampling occurred within 3 weeks after the incident.

This example shows the in vivo effect on DNA damage in HML following the per os administration of CNZ (carotenoids+nicotinamide+zinc) in relation to Commercial Product I (CPI, containing carotenoids+nicotinamide+zinc+17 other supplements) when evaluated in the same individuals (FIG. 7). Here the data demonstrate that although CNZ supplementation resulted in a significant resistance to the induction of DNA damage from a standardized in vitro dose of hydrogen peroxide in HML of Cases B and C compared to the control, CPI supplementation had no such effect (i.e. in this material compared to individuals labeled control and Case A). This experiment teaches that the presence of other natural products in addition to carotenoids+nicotinamide+zinc in the supplementation limits the biological effectiveness on cellular resistance to DNA damage for these 3 compounds given in exclusive combination.

EXAMPLE 7

Figure 8:
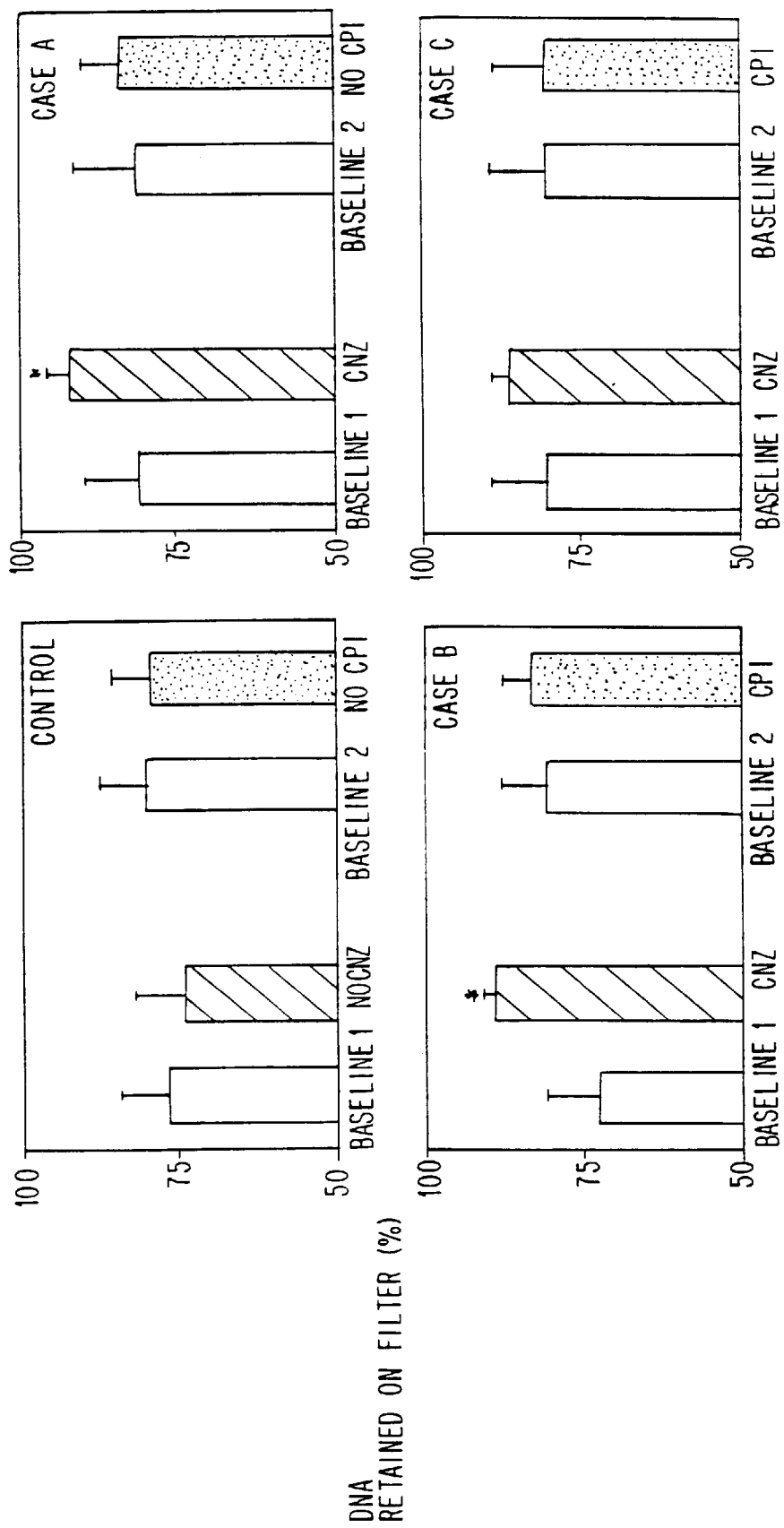
FIG. 8 is a set of bar graphs comparing the in vivo effect of carotenoids+nicotinamide+zinc supplementation in accordance with the invention ("CNZ"), and the aforementioned Commercial Product I supplement ("CPI"), on DNA repair in human mononuclear leukocytes. The DNA repair was assessed by alkaline elution 60 minutes after DNA damage induced by 100 $\mu$M hydrogen peroxide. The data are expressed as mean in column and SD by error bar (n=4 to 5 for each column). * indicates a significant difference ($p<0.05$, t-test) compared with corresponding baseline levels. § Note: Case A was not supplemented with Commercial Product I because of acute appendicitis just as the supplement started, and no blood sampling occurred within 3 weeks after the incident.

This example shows the in vivo effect on DNA repair in HML following the per os administration of CNZ (carotenoids+nicotinamide+zinc in relation to CPI (carotenoids+nicotinamide +zinc+17 other supplements) when evaluated in the same individuals (FIG. 8). Case B establishes that when CNZ supplementation significantly enhanced DNA repair, there was no corresponding effect when the same individual was supplemented with CPI or not supplemented at all (i.e. in this material compared to individuals labeled control and Case A). This experiment teaches that the presence of other natural products in addition to carotenoids+nicotinamide+zinc in the supplementation limits the biological effectiveness on DNA repair for these 3 compounds given in exclusive combination.

EXAMPLE 8

Figure 9:
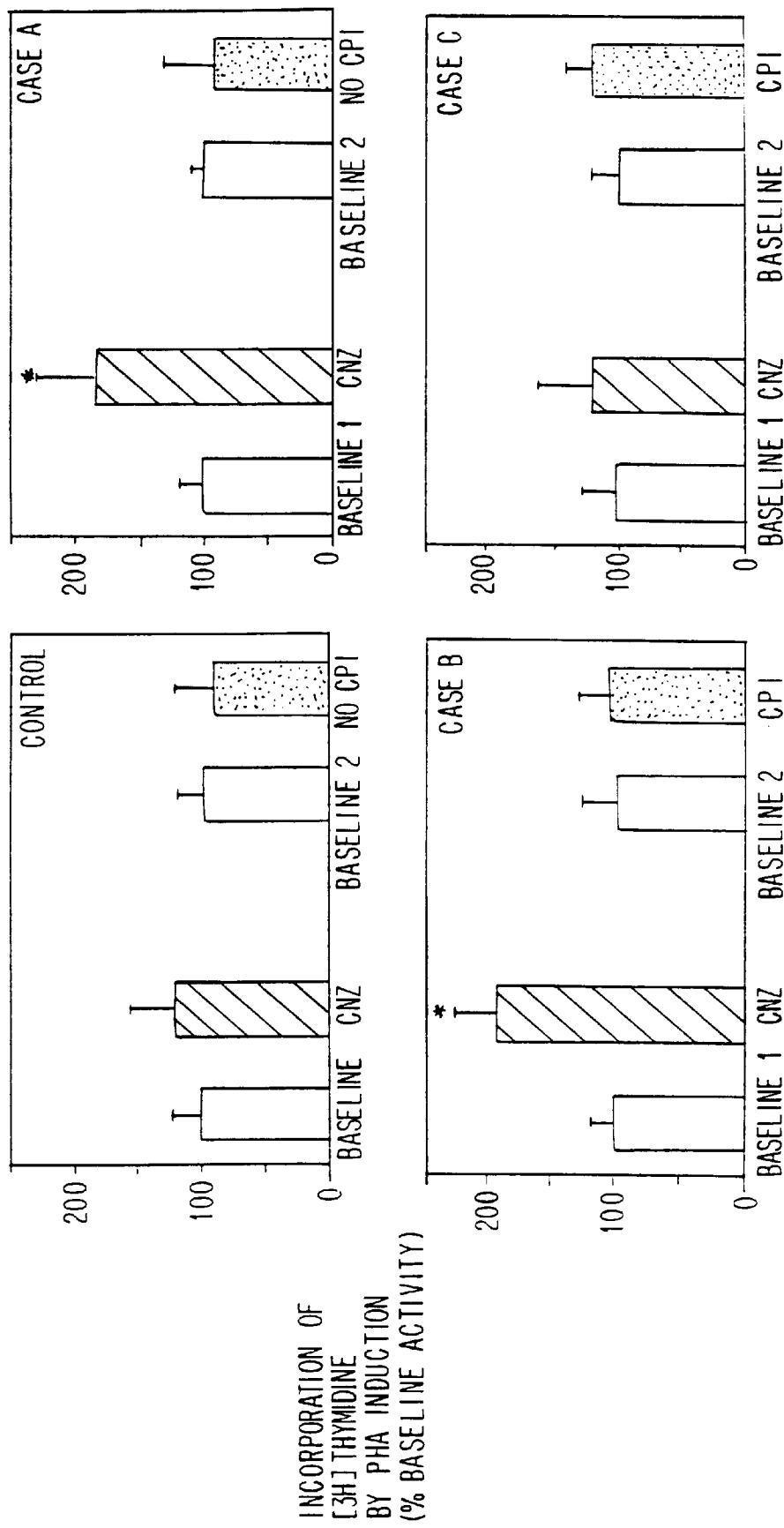
FIG. 9 is a set of bar graphs comparing the in vivo effect of carotenoids+nicotinamide+zinc supplementation in accordance with the invention ("CNZ"), and the aforementioned Commercial Product I supplement ("CPI"), on human lymphocyte stimulation by PHA. The results are expressed as % of baseline level (mean in bar and SD in error bar). * indicates a significant difference ($p<0.05$) compared with corresponding baseline level. § Note: Case A was not supplemented with Commercial Product I because of acute appendicitis just as the supplement started, and no blood sampling occurred within 3 weeks after the incident.

This example shows the in vivo effect on immune responsiveness in HML treated in vitro with the mitogen, phytohemagluttinin (PHA), following the per os administration of CNZ (carotenoids+nicotinamide+zinc) in relation to CPI (carotenoids+nicotinamide+zinc+17 other supplements) when evaluated in the same individuals (FIG. 9). Case B establishes that when Nicoplex supplementation significantly enhanced HML stimulation by PHA, there was no corresponding effect when the same individual was supplemented with CPI or not supplemented at all (i.e. in this material compared to individuals labeled control and Case A). This experiment teaches that the presence of other natural products in addition to carotenoids+nicotinamide+zinc in the supplementation limits the biological effectiveness on immune cell responses for these 3 compounds given in exclusive combination.

It is to be understood that the invention is not limited to the features and embodiments hereinabove specifically set forth, but may be carried out in other ways without departure from its spirit.

What is claimed is:

1. A composition of matter for administration to humans or other animals, consisting essentially of a combination of carotenoid material, nicotinamide material and zinc source material and essentially free of other active ingredients.

2. A composition as defined in claim 1, in a formulation for oral administration.

3. A composition as defined in claim 1, in a formulation for parenteral administration.

4. A composition as defined in claim 1, wherein said carotenoid material is selected from the group consisting of alpha carotene, beta carotene, gamma carotene, lycopene and mixtures thereof.

5. A composition as defined in claim 1, wherein said nicotinamide material is selected from the group consisting of nicotinamide, niacin, tryptophane and mixtures thereof.

6. A composition as defined in claim 1, wherein said zinc source material is one or more zinc salts.

7. A composition as defined in claim 6, wherein said carotenoid material is selected from the group consisting of alpha carotene, beta carotene, gamma carotene and lycopene and mixtures thereof, and said nicotinamide material is selected from the group consisting of nicotinamide, niacin and tryptophane and mixtures thereof.

8. A composition as defined in claim 1, wherein said carotenoid material, nicotinamide material and zinc source material are present in proportions effective, in said combination, to improve resistance to DNA damage, enhance DNA repair capacity, and stimulate immune function in a human subject to whom the composition is administered as a daily dosage.

9. A method of treating a human or other animal subject, consisting of the steps of (a) administering carotenoid material, nicotinamide material and zinc source material to the subject to selectively supplement the subject's dietary intake thereof and (b) repeating step (a) substantially daily.

10. A method according to claim 9, wherein about 100 mg of carotenoid material, about 100 mg of nicotinamide material and about 10 mg of zinc source material are administered in step (a).

11. A method of treating a human subject consisting of selectively administering to the subject carotenoid material, nicotinamide material and zinc source material, said materials being administered to the subject in daily dosage amounts effective, in combination, to improve resistance to DNA damage, enhance DNA repair capacity, and stimulate immune function.

12. A composition of matter for administration to humans or other animals, consisting essentially of a plurality of active nutrient agents respectively having different and non-competitive modes of action and essentially free of other active ingredients.

13. A method of treating a human or other animal subject, consisting of administering to the subject, in combination, a plurality of active nutrient agents respectively having different and non-competitive modes of action.

* * * * *